United States Patent [19]

Philion

[11] Patent Number: 5,672,702
[45] Date of Patent: Sep. 30, 1997

[54] PROCESS FOR PREPARING 3 AMINO 1, 2, 4-BENZOTRIAZINE DIOXIDE

[75] Inventor: Richard E. Philion, Pottstown, Pa.

[73] Assignee: Sanofi, Paris Cedex, France

[21] Appl. No.: 566,979

[22] Filed: Dec. 4, 1995

[51] Int. Cl.⁶ .............................................. C07D 253/065
[52] U.S. Cl. ........................................................... 544/183
[58] Field of Search ............................................... 544/183

[56] References Cited

U.S. PATENT DOCUMENTS

| | | | |
|---|---|---|---|
| 3,868,371 | 2/1975 | Ley et al. | 260/249.5 |
| 3,957,779 | 5/1976 | Seng et al. | 424/249 |
| 3,980,779 | 9/1976 | Ley et al. | 424/249 |
| 3,991,189 | 11/1976 | Seng et al. | 424/249 |
| 5,175,287 | 12/1992 | Lee et al. | 544/183 |
| 5,484,612 | 1/1996 | Brown | 424/649 |

FOREIGN PATENT DOCUMENTS

| | | | |
|---|---|---|---|
| 8802366 | 4/1988 | WIPO . | |
| 9104028 | 4/1991 | WIPO | A61K 31/53 |

OTHER PUBLICATIONS

Seng F. et al "Simple Synthesis of 3-Amino-1,2-4-Benzatriozine". Angew. Chem. 84, 1061, (1972).

*Primary Examiner*—Mukund J. Shah
*Assistant Examiner*—Sabiha Qazi
*Attorney, Agent, or Firm*—William J. Davis; Imre Balogh

[57] ABSTRACT

Process of producing 3-amino-1,2,4-benzotriazine 1,4-dioxide by reacting benzofurazan-1 oxide with disodiumcyanamide under homogeneous conditions followed by allowing crystallization to occur in a buffered solution. In a preferred embodiment, the process comprises reacting benzofurazan-1 oxide with cyanamide and sodium hydroxide under homogeneous conditions followed by purification in a mixture of acetone and acetic acid.

7 Claims, No Drawings

PROCESS FOR PREPARING 3 AMINO 1, 2, 4-BENZOTRIAZINE DIOXIDE

BACKGROUND OF THE INVENTION

1. Field of the Invention

This invention relates to a process for the preparation of 3-amino-1,2,4-benzotriazine dioxide (hereinafter sometimes referred to as tirapazamine) of high purity for systemic administration for the treatment of cancer tumors in mammals.

2. Reported Developments

Tirapazamine is a known compound having been reported in U.S. Pat. No. 3,868,371 for use as antimicrobial and in U.S. Pat. No. 3,957,779 where it and its family of compounds are disclosed for use as growth promoting in raising fatstock animals, such as cattle, pigs and poultry. Tirapazamine also is a promising drug as an anticancer tumor agent in mammals as disclosed in WO 91/04028, the description of which is incorporated herein by reference. In using tirapazamine systemically, it is important that the compound is highly purified so as to obtain its desired anticancer tumor activity without side effects due to impurities that may remain in the compound during its manufacture.

The process of preparing tirapazamine is disclosed in Angew. Chem. 84, 1061 (1972) and in U.S. Pat. No. 3,868,371 as follows.

(Disodium cyanamide)

is reacted with

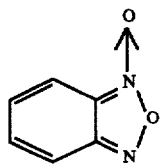

Benzofuroxan in the presence of

to obtain the sodium salt thereof

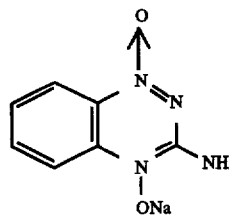

which, on acidification with acetic acid, is transformed into

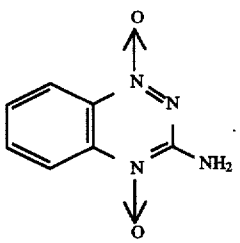

3-amino-1,2,4-benzotriazine 1,4-dioxide

The details of the process is reproduced herein.

To a suspension of 13.6 g (0.1 mol) of benzofuroxan in a mixture of 40 ml of methanol and 40 ml of water at 20° C. are added in portions 17.2 g (0.2 mol) of disodium cyanamide. In the course of addition, the temperature rises to 50° C.–60° C. and the solution assumes a blue-violet color. It is stirred for a further 40 minutes at about 60° C. and the precipitate which separates out is then removed by filtration from the mother liquor, which is retained and processed further. The precipitate is dissolved in water, the solution is filtered and the filtrate is acidified with acetic acid, whereupon 12.5 g of 3-amino-1,2,4-benzotriazine-1,4,-di-N-oxide (71% of theory) separates out in the form of reddish-golden crystals which melt, with decomposition, at 220° C. On acidifying the mother liquor with acetic acid, a further 3.2 g (18% of theory) of 3-amino-1,2,4-benzotriazine is obtained and after re-crystallization from dimethylformamide, this material melts, with decomposition, at 220° C. Total yield reported is: 89% of theory.

I have now discovered an improved process for producing 3-amino-1,2,4-benzotriazine 1,4-dioxide.

SUMMARY OF THE INVENTION

The process of preparing 3-amino-1,2,4-benzotriazine 1,4-dioxide comprises the steps of:

a) dissolving benzofurazan-1 oxide in dimethylsulfoxide in a molar ratio of 1 to 3;

b) dissolving disodiumcyanamide in water in a molar ratio of 3 to 2 contained in a reaction flask;

c) adding the benzofurazan-1 oxide solution to the disodiumcyanamide solution at a temperature of from about 55° C. to 65° C., and preferably at about 60° C. to obtain the sodium salt of 3-amino-1,2,4-benzotriazine 1,4-dioxide as a precipitate;

d) removing the precipitate by filtration;

e) suspending the filtrate in water in a volume of about 1 to 6;

f) adding about 3.5 mole equivalents of methanesulfonic acid to the suspended filtrate to obtain a solution;

g) filtering the solution to remove acid insoluble impurities therefrom;

h) charging the filtered solution into a buffer solution containing excess sodium acetate;

i) allowing crystallization to occur forming crystalline particles more than 90% of which have a particle size of less than 190 nm;

j) filtering and washing the crystalline particles with water;

k) charging the washed crystalline particles back into said reaction flask and stirring with about five volumes of water; and l) filtering the crystalline particles and rinsing them with acetone to obtain the purified 3-amino-1,2,4-benzotriazine 1,4-dioxide.

The purified product may be dried at about 50° to 60° C. and made homogeneous by passing it through a No. 10 stainless steel sieve which then is ready for use in a solid oral pharmaceutical formulation, such as in a soft gel capsule.

In a preferred embodiment of the invention the process of preparing 3-amino-1,2,4-benzotriazine 1,4-dioxide comprises the steps of:

a) adding a solution of benzofurazan-1 oxide in dimethylsulfoxide in a molar ratio of 1 to 3 to an aqueous solution of cyanamide and sodium hydroxide having a molar ratio of 3 to 6 at a temperature of from about 55° C. to 65° C. to obtain the sodium salt of 3-amino-1,2, 4-benzotriazine 1,4-dioxide as a partial suspension/solution;

b) diluting the partial suspension/solution with water in a volume ratio of about 1 to 6 thereby obtaining a solution containing base-insoluble impurities;

c) filtering the solution to remove the base-insoluble impurities therefrom;

d) neutralizing the solution with a slight excess of glacial acetic acid to obtain a crude crystalline mixture;

e) cooling the crystalline mixture and collecting the solids by filtration in the form of a damp cake;

f) adding, with stirring, a mixture of acetone and acetic acid in the ratio of about 88: 12;

g) collecting the crystalline particles by filtration and rinsing them with the mixture of acetone and acetic acid having the ratio of about 88: 12, followed by rinsing with water;

h) adding about five volumes of water to the crystalline particles to obtain a suspension;

i) acidifying the suspension with methanesulfonic acid in a 3.5 mol equiv. ratio;

j) collecting the suspended crystalline particles by filtration, charging them into a well-stirred dilute sodium acetate solution, and allowing them to microcrystallize to form an average particle size of less than 190 mm; and k) collecting the microcrystalline particles by filtration and rinsing them with water, followed by rinsing with acetone to obtain the purified 3-amino-1,2,4-benzotriazine 1,4-dioxide.

The purified product may be dried at about 50° to 60° C. and made homogeneous by passing it through a No. 10 stainless steel sieve which then is ready for use in a solid oral pharmaceutical formulation, such as in a soft gel capsule. If aggregation occurs, a milling step may be used in the process of the present invention to insure homogeneity of the microcrystalline particles prior to their incorporation in soft gel capsules. Preferably, the milling should be done by a low energy comill to avoid high impact and heat problems.

DETAILED DESCRIPTION OF THE INVENTION

Tirapazamine is a potent cytotoxic agent that was shown to have enhanced toxicity and selectivity toward hypoxic cells that exist in cancerous tumors. Its efficacy was observed with both parenteral and solid form oral preparations. One of the objects of the present invention is to provide tirapazamine in a particle size suitable for solid oral preparations without the necessity to reduce the particle size subsequent to the synthesis of tirapazamine.

In order to obtain highly pure tirapazamine for use in such pharmaceutical preparations, extensive studies were conducted to improve the process and the resultant product reported in Angew. Chem. 84, 1061 (1972) and in U.S. Pat. No. 3,868,371, as described hereunder.

Heterogeneous Reaction Conditions

Example 1

The process described by the references was repeated with modifications as described in Examples 1–4.

The heterogeneous reaction of one mole of benzofurazan 1-oxide with three moles of disodiumcyanamide in 50% aqueous methanol is immediately exothermic. According to the cited references, the preferred sequence is to suspend the benzofurazan-1 oxide and two moles of disodiumcyanamide in aqueous methanol. After several minutes another mole of disodium-cyanamide was added to the reaction mixture. Shortly afterward, the intermediate sodium salt precipitated out as a black-violet buttery solid. The wet solid was difficult to transfer form a conventional reaction flask and the filtration was slow and cumbersome. The crude precipitate was dissolved in water and filtered to remove base-insoluble impurities. The filtrate was acidified with acetic acid and the product was isolated as an orange-colored solid: the product was dissolved in approximately 10 volumes of acetic acid at 80° C., but did not crystallize readily unless concentrated or, alternatively, diluted with a less polar solvent.

Example 2

The same process was used as in Example 1 except, the intermediate black-violet buttery solid was dissolved and acidified without filtration. The recovery was high but an impurity was observed by TLC that was very difficult to remove by chromatography. The impurity was isolated by flash chromatography and identified as phenazine 1,5-di-N-oxide. This compound is the most abundant byproduct in the reaction and arises form a self-condensation of benzofurazan-1 oxide.

Example 3

The process of Example 1 was followed to obtain the crude product except 2 moles of benzofurazan-1 oxide was reacted with 6 moles of disodiumcyanamide. Upon addition of the two solutions vigorous exothermic reaction occurred accompanied by gas evolution. The yield after work-up was reduced to 22%.

Example 4

The process of Example 1 was followed to obtain the crude product except 1.2 moles of benzofurazan-1 oxide was reacted with 3.6 moles of disodiumcyanamide. Upon removing the precipitated crude product, it was suspended in water and 35% sodium hydroxide was added until a solution developed. The solution was filtered and acidified with acetic acid to give the crystalline product. The product was found to contain the impurity, mono-N-oxide of phenazine. Also, the product contained a floc that could only be removed by filtration from acetic acid at a temperature of 85° C. The manipulation of the hot solution of the cytotoxic agent was found to be a serious drawback.

To eliminate the drawbacks and undesirable characteristics of the process of the references and the final product obtained thereby, substantial studies were conducted in order to select the best experimental conditions and reagents for use in an improved process.

Homogeneous Reaction Conditions

1. Solvent

The solubility characteristics of the reagents limited the choice of solvent for conducting experiments under homogeneous reaction conditions. Benzofurazan-1 oxide is very soluble in non-polar solvents such as toluene or ethyl acetate. It is much less soluble in isopropanol or methanol. However, it is very soluble in polar aprotic solvents such as dimethylformamide, N-methylpyrrolidinone or dimethylsulfoxide (DMSO). One mole of benzofurazan-1 oxide readily dissolves endothermically in 3 volumes of DMSO at room temperature.

Disodiumcyanamide is insoluble in organic solvents, but dissolves exothermically in water. Three moles can be dissolved in two volumes of water to give sodium cyanamid which is in equilibrium with sodium hydroxide.

The strongly caustic reaction medium was a limiting factor to the selection of a solvent for benzofurazan-1 oxide. Dimethylsulfoxide was chosen over dimethylformamide because of its proven stability in a strong base.

2. Mode of Addition

Normal addition was defined as the addition of a solution of benzofurazan-1 oxide in DMSO to a solution of excess disodiumcyanamide in water. In one experiment where an aqueous solution of disodiumcyanamide was added to a solution of benzofurazan-1 oxide in methanol, a low recovery of product was observed and the major byproduct form this reaction was identified as phenazine mono-N-oxide. Under conditions where an excess of benzofurazan-1 oxide is present, as in the inverse addition, the formation of phenazine related byproducts is favored.

3. Stoichiometry

According to the literature (Angew. Chem. Int. Ed., Vol. 11 (1972) 1009) and based on our research using heterogeneous reaction conditions, the preparation of tirapazamine requires 3 equivalents of disodiumcyanamide for every equivalent of benzofurazan-1 oxide. In one experiment where one mole equivalent was reacted with 2 mole equivalents under homogeneous conditions, a 26% recovery of starting benzofurazan-1 oxide as obtained. The thermal stability of aqueous solutions of sodiumcyanamide is well known, but at elevated temperatures hydrolysis to cyanate and liberation of ammonia is known to occur. Cyanamide is also known to polymerize to a dimeric species and to the water insoluble trimer, melamine.

Several homogeneous reactions were carried out using cyanamide and benzofurazan-1 oxide in DMSO and water. The formation of product was comparable to disodiumcyanamide, but only when three moles of cyanamide and six moles of sodium hydroxide were used.

4. Temperature

Under standard reaction conditions, a solution of benzofurazan-1 oxide in DMSO at room temperature is added to a solution of disodiumcyanamide in water. The yield of product was optimum when the temperature of the disodiumcyanamide solution was maintained between 55°–60° C. during the addition. The reaction proceeded rapidly at this temperature and no apparent exotherm was observed. In one experiment where the temperature was maintained at 34°–40° C., the starting benzofurazan-1 oxide was recovered in 40% yield. The details of this experiment and other experiments that demonstrated reproducibility at the optimum reaction temperature are shown in Table 1.

TABLE 1

| Code | Moles A* | Moles B* | Reaction Temperature | Crude Yield | Recov. Start |
|---|---|---|---|---|---|
| 1736-051 | 1 | 3 | 34–40_ | 38% | 40% |
| 1736-049 | 1 | 3 | 60–95_ | 48% | — |
| 1736-054 | 0.1 | 0.2 | 58–60_ | 31% | 29% |
| 1736-052 | 1 | 3 | 55–60_ | 65% | — |
| 1736-057 | 1 | 3 | 58–62_ | 65% | — |
| 1736-061 | 1 | 3 | 56–58_ | 56% | — |

A* = Benzofurazan-1 oxide
B* = Disodiumcyanamide

5. Ratio of Solvent

Most of the experiments were carded out in approximately 1:1 DMSO/water. In one experiment where a 1:2 ratio of DMSO/water was used, a slightly higher recovery of starting benzofurazan-1 oxide was noted and the yield of tirapazamine was correspondingly lower. Most of the reactions were carried out in 7:1 volume to weight ratio base on benzofurazan-1 oxide.

When solvents such as isopropanol or THF were substituted for DMSO, the reaction gave predominately the starting material even after prolonged heating.

6. Crystallization

The purification of crude tirapazamine was achieved by dissolving the crude tirapazamine in 9 volumes of acetic acid at 80°–90° C. The mixture was filtered to remove insoluble impurities and the filtrate was concentrated under a partial vacuum to one half the original volume at 60° C. Avoidance of the crystallization from acetic acid or form acidic solutions has consistently led to problems with floc. The identification of the floc has not been determined. Filtration of flocculent solutions gave only a stain on the filter paper and insufficient solid to characterize by ordinary spectroscopic methods.

To avoid a distillation step, more concentrated solutions could be prepared at 106° from 6 volumes of acetic acid. Although feasible, this was considered to be a potential hazard.

Suspensions containing 9 g of tirapazamine in 50 ml water were prepared and three acids (methanesulfonic, sulfuric and hydrochloic) were chosen to examine their respective solubility properties. The methanesulfonic acid solution appeared the most promising and the free base was isolated after neutralization with sodium hydroxide. The crystals form this procedure were examined for particle size and did not meet the specification of 90%<190 nm.

The exotherm from the neutralization with sodium hydroxide prevented the rapid addition that was thought to be necessary for the generation of crystals with the desired particle size. This problem was addressed by quenching the acidic solution into a cold sodium acetate buffer which moderated the exotherm and allowed for a very rapid addition. The crystals obtained in this manner met the particle size specification. The recoveries and initial examination by TLC and HPLC gave an impurity profile very similar to that obtained from acetic acid. More importantly, no evidence of floc could be observed from acetic acid solutions that were left standing overnight.

Using homogeneous reaction parameters obtained by the studies, tirapazamine was prepared as described in Example 5.

Example 5

Seven reactions were carded out ranging in scale from one, two and three moles of benzofurazan-1 oxide and form corresponding three, six and nine moles of disodiumcyanamide, as shown in Table 2.

The solution of benzofurazan-1 oxide in dimethylsulfoxide in a molar ratio of 1 to 3 was added to an aqueous solution of disodiumcyanamide having a molar ratio of 3 to 2 at about 60° C. contained in a reaction vessel. The addition time varied form 8 to 34 minutes and the sodium salt of the product precipitated several minutes after the addition was completed. The precipitate was removed by filtration and was suspended in water in a volume ratio of about 1 to 6. The suspension contains base insoluble material and therefore it is filtered to remove the same. To the suspension was added about 3.5 mole equivalents of methanesulfonic acid at room temperature. The temperature rose to about 45° C. and the warm solution was filtered to remove acid insoluble impurities. The filtrate then was charged into a buffer containing excess sodium acetate. Rapid crystallization occurred with 90% of the crystals having a particle size of less than 190 nm. The crystalline particles were filtered and washed well with water. The crystalline particles, in the form of a damp cake, was charged back into the reaction vessel and stirred with about five volumes of water. After washing, the solids were filtered and rinsed with acetone to obtain the purified tirapazamine. The purified material was dried for three days at about 50° to 60° C. The dried solid was made homogeneous by passing it through a No. 10 stainless steel sieve.

The yield and assay results are shown in Table 2.

TABLE 2

| Code | Moles A* | Moles B* | Crude Recovery | Yield | ETI | LOD | Assay |
| --- | --- | --- | --- | --- | --- | --- | --- |
| 1736-077 | 1 | 3 | 123 g | 69% | 0.18 | 2.6 | 92.7% |
| 1736-078 | 2 | 6 | 241 g | 68% | 0.15 | 3.2 | 94.5% |
| 1736-080 | 2 | 6 | 224 g | 63% | 0.14 | 5.4 | 98.5% |
| 1736-082 | 2 | 6 | 247 g | 69% | 0.92 | 5.5 | 93.1% |
| 1736-084 | 2 | 6 | 246 g | 69% | 0.79 | 8.2 | 91.8% |
| 1736-086 | 3 | 9 | 318 g | 60% | 0.82 | 2.3 | 92.4% |
| 1736-088* | 1 | 3 | 116 g | 65% | 0.91 | 0.7 | 96.2% |

A* = moles of benzofurazan-1 oxide
B* = moles of disodiumcyanamide

The process was successfully repeated on 4 and 15 mole scales to provide kilo quantities of tirapazamine in pure form. The process meets the criteria of safety and reproducibility. The product so produced in the form of crystalline, nanometer size necessary for solid oral formulation used in the treatment of cancer tumors.

The process of the preferred embodiment of the present invention is shown in Examples 6 and 7.

Example 6

To an aqueous solution containing about six moles of sodium hydroxide at 20°–30° C. was added about three moles of cyanamide. The mixture was stirred for about 1 hour at room temperature and then warmed to about 60° C. A solution containing one mole of benzofurazan-1 oxide (calculated on a dry weight basis) in dimethyl sulfoxide was added to the basic cyanamide mixture over 10–20 minutes. At the end of the addition, an exotherm developed which was kept below 75° C. by cooling. The mixture was diluted with deionized water and the insoluble by-products were removed by filtration at about 45° C. The combined filtrate and washes were acidified with glacial acetic acid. The crystalline mixture was cooled and the solids were collected by filtration. The cake was rinsed with deionized water and the damp solids were transferred to a clean reaction vessel.

The damp solids were diluted with a mixture of acetone and acetic acid in the approximate ratio of 88:12. The mixture was stirred at room temperature for about 30 minutes. The solids were collected by filtration. The cake was also rinsed with the solution of acetone and acetic acid (88:12) and then with deionized water. The damp cake was transferred to a clean reaction vessel.

Final Purification

The damp solids were diluted with deionized water and the suspension was acidified with dilute methanesulfonic acid. The mixture was treated with charcoal and stirred for several minutes at about 45° C. The mixture was filtered warm and the charcoal treatment was repeated a second time. After filtration, the warm filtrate was charged to a well-stirred, cold solution of dilute sodium acetate. The solids were collected by filtration. The cake was rinsed with deionized water and then with acetone. The crystalline solid was vacuum dried at about 55° C. to afford the pure product.

The overall yield was about 40–50% of theory.

Example 7

This example describes the process of producing a large, batch-size quantity of 1,2,4-benzotriazine-3-amino 1, 4-dioxide.

A 50 gal reactor (K-7) was purged with nitrogen and charged with a 17.9L deionized water and 11.9 Kg (297 moles) sodium hydroxide beads. Cooling was employed to control the exotherm. The mixture was agitated until a clear solution was obtained and then cooled to 15°–25° C. The solution was charged with 6.3 Kg (150 moles) cyanamide and stirred for 1 hour at 20°–30° C. In the meantime, another kettle (K-5) was charged with 7.4 Kg damp benzofurazan 1-oxide (7.0 Kg calculated on a dry basis) (50 moles) and 25.5 Kg dimethyl sulfoxide. The mixture was stirred with warming to 20°–30° C. for 50 minutes.

The cyanamide solution (K-7) was warmed to 60° C. The benzofurazan 1-oxide (K-5) was transferred through an in-line cartridge filter to the cyanamide solution over approximately 20 minutes. The reaction mixture was stirred with cooling for another 20 minutes and the temperature did not exceed 71° C. Deionized water (50L) was gradually added to the reaction. The mixture was cooled to 44° C. and the insoluble by-products were removed through an in-line cartridge filter which discharged the filtrate into a 50 gal reactor (K-8). The filtrate was acidified by the addition of 19.9 Kg (332 moles) acetic acid. The mixture was cooled to 22° C. and agitation was continued for 1 hour. The solids were collected by filtration. The reactor (K-8) was rinsed with 17.3L deionized water and applied to the filter cake. The damp cake was transferred to a 50 gal reactor (K-8).

A solution containing 34.9 Kg acetone and 6.0 Kg acetic acid was prepared and charged to the crude solid in K-8. The mixture was stirred at 25° C. for 3 hours and the solids were collected by filtration. The cake was rinsed with a solution containing 10.4 Kg acetone and 1.8 Kg acetic acid. The reactor (K-8) was charged with 15.0L deionized water and was used to wash the cake. The crude, damp cake was used in the final purification step.

A 50 gal reactor (K-8) was charged with 11.6 Kg (141.5 moles) of anhydrous sodium acetate and 61.5L deionized water. The mixture was stirred and the clear solution was cooled to 10°–20° C.

In the meantime, a 30 gal reactor CK-11) was purged with nitrogen and charged with 35.9L deionized water and 7.7 Kg of the crude, damp Tirapazamine. The suspension was stirred for 20 minutes and 10.0 Kg (102 moles) methanesulfonic acid was added over several minutes. The temperature was adjusted to 40°–45° C. and 0.2 Kg of activated charcoal and 0.2 Kg of solka floc was added to the dark solution. The mixture was circulated through an in-line filter to remove the solids. The activated charcoal and solka floc step was repeated a second time. The filtrate was circulated through a polishing filter and rapidly charged to the cold sodium acetate solution (K-8). The mixture was stirred with cooling for about 1.5 hours and the solids were collected by filtration at 10° C. The deionized water (34 Kg) charged to the reactor (K-8) was used to wash the filter cake. The cake was given a final rinse with 17.9 Kg of acetone and vacuum dried at 55°–60° C. for 43 hours. The weight of the pure product was 3.41 Kg (37.2% yield of theory).

Having described the invention with reference to its preferred embodiments, it is to be understood that modifications within the scope of the invention will be apparent to those skilled in the art.

What is claimed is:

1. A process for the preparation of 3-amino-1,2,4-benzotriazine 1,4-dioxide comprising the steps of:
    a) adding a solution of benzofurazan-1 oxide in dimethylsulfoxide in a molar ratio of 1 to 3 to a solution of disodiumcyanamide in water in a molar ratio of 3 to 2 contained in a reaction vessel at a temperature of from about 55° to 65° C. to obtain the sodium salt of 3-amino-1,2,4-benzotriazine 1,4-dioxide as a precipitate;
    b) removing the precipitate and suspending it in excess water;
    c) adding about 3.5 mole equivalents of methanesulfonic acid to the suspension to obtain a solution;
    d) filtering the solution to remove acid insoluble impurities therefrom;
    e) charging the filtered solution into a buffered solution containing excess sodium acetate and allowing crystallization to occur;
    f) filtering and washing the crystalline particles with water;
    g) charging the washed crystalline particles back into said reaction vessel and stirring it with about five volume of water; and
    h) filtering the crystalline particles and rinsing them with acetone to obtain the purified 3-amino-1,2,4-benzotriazine 1,4-dioxide.

2. The process of claim 1 further comprising: drying and homogenizing the purified 3-amino-1,2,4-benzotriazine 1,4-dioxide.

3. The process of claim 1 wherein said benzofurazan-1 oxide is added to said disodiumcyanamide solution at a temperature of about 60° C.

4. The process of claim 1 wherein in step (b) the filtrate is suspended in water in a volume ratio of 1 to 6.

5. A process for the preparation of 3-amino-1,2,4-benzotriazine 1,4-dioxide comprising the steps of:
    a) adding a solution of benzofurazan-1 oxide in dimethylsulfoxide in a molar ratio of 1 to 3 to an aqueous solution of cyanamide and sodium hydroxide having a molar ratio of 3 to 6 at a temperature of from about 55° C. to 65° C. to obtain the sodium salt of 3-amino-1,2,4-benzotriazine 1,4-dioxide as a partial suspension/solution;
    b) diluting the partial suspension/solution with water in a volume ratio of about 1 to 6 thereby obtaining a solution containing base-insoluble impurities;
    c) filtering the solution to remove the base-insoluble impurities therefrom;
    d) neutralizing the solution with a slight excess of glacial acetic acid to obtain a crude crystalline mixture;
    e) cooling the crystalline mixture and collecting the solids by filtration in the form of a damp cake;
    f) adding, with stirring, a mixture of acetone and acetic acid in the ratio of about 88: 12;
    g) collecting the crystalline particles by filtration and rinsing them with the mixture of acetone and acetic acid having the ratio of about 88: 12, followed by rinsing with water;
    h) adding about five volumes of water to the crystalline particles to obtain a suspension;
    i) acidifying the suspension with methanesulfonic acid in a 3.5 mol equiv. ratio;
    j) collecting the suspended crystalline particles by filtration, charging them into a well-stirred dilute sodium acetate solution, and allowing them to microcrystallize to form an average particle size of less than 190 mm; and
    k) collecting the microcrystalline particles by filtration and rinsing them with water, followed by rinsing with acetone to obtain the purified 3-amino-1,2,4-benzotriazine 1,4-dioxide.

6. The process of claim 5 further comprising: drying and homogenizing the purified 3-amino-1,2,4-benzotriazine 1,4-dioxide.

7. The process of claim 6 wherein said benzofurazan-1 oxide is added to said cyanamide solution at a temperature of about 60° C.

* * * * *